United States Patent
Sanger

(10) Patent No.: US 9,326,847 B2
(45) Date of Patent: May 3, 2016

(54) OCULAR IMPLANT INSERTION APPARATUS AND METHODS

(75) Inventor: Demas Sanger, Fukaya (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 13/583,216

(22) PCT Filed: Apr. 6, 2011

(86) PCT No.: PCT/JP2011/059131
§ 371 (c)(1),
(2), (4) Date: Sep. 18, 2012

(87) PCT Pub. No.: WO2011/126144
PCT Pub. Date: Oct. 13, 2011

(65) Prior Publication Data
US 2013/0006259 A1    Jan. 3, 2013

(30) Foreign Application Priority Data
Apr. 8, 2010   (JP) ................. 2010-089186

(51) Int. Cl.
*A61F 9/00*   (2006.01)
*A61F 2/16*   (2006.01)

(52) U.S. Cl.
CPC .................... *A61F 2/1672* (2013.01)

(58) Field of Classification Search
CPC ...... A61F 2/167; A61F 2/1678; A61F 2/1672
USPC .............. 606/107, 166, 170, 171; 623/6.162; 215/218; 411/291, 294
See application file for complete search history.

(56) References Cited

U.S. PATENT DOCUMENTS

| 2,761,446 | A | 9/1956 | Reed |
| 4,205,747 | A | 6/1980 | Gilliam et al. |
| 4,269,307 | A | 5/1981 | LaHaye |
| 4,423,809 | A | 1/1984 | Mazzocco |
| 4,573,998 | A | 3/1986 | Mazzocco |

(Continued)

FOREIGN PATENT DOCUMENTS

| DE | 3610925 | 10/1987 |
| DE | 4110278 | 10/1992 |

(Continued)

OTHER PUBLICATIONS

PCT International Preliminary Examination Report dated Oct. 18, 2012 in corresponding PCT App. Ser. No. PCT/JP2011/059131.

(Continued)

*Primary Examiner* — Richard Louis
(74) *Attorney, Agent, or Firm* — Henricks, Slavin & Holmes LLP

(57) ABSTRACT

Ocular implant insertion apparatus configured for screw-type and push-type operation and associated methods. Such insertion apparatus includes a main body defining a longitudinal axis and a plunger, movable relative to the main body, including a rod portion and an operational portion rotatably mounted on the rod portion. One of the main body and the plunger operational portion includes a helical slot and at least one longitudinally extending clearance groove that intersects the helical slot and the other of the main body and the operational portion includes at least one protrusion that is sized and shaped to fit within the helical slot and within the at least one longitudinally extending clearance groove.

20 Claims, 10 Drawing Sheets

(56) References Cited

U.S. PATENT DOCUMENTS

| | | |
|---|---|---|
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A * | 3/1989 | Haber et al. .................. 604/210 |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A * | 11/1993 | Li .................................. 607/131 |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,591,136 A * | 1/1997 | Gabriel ......................... 604/211 |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A * | 7/1997 | Chanoch ....................... 604/189 |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A * | 3/1998 | Levander ...................... 604/211 |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A * | 9/1998 | Chambers et al. ............ 606/107 |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A * | 9/1999 | Bendek et al. ................ 604/207 |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |

(56) References Cited

U.S. PATENT DOCUMENTS

| | | |
|---|---|---|
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Wadlaock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1* | 5/2003 | Seil .................. 606/107 |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0186428 A1* | 9/2004 | Ray .................. 604/110 |
| 2004/0210199 A1* | 10/2004 | Atterbury et al. .......... 604/224 |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1* | 3/2005 | Enggaard .................. 604/500 |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0200167 A1 | 9/2006 | Peterson et al. |
| 2006/0229633 A1* | 10/2006 | Shepherd .................. 606/107 |
| 2006/0235429 A1 | 10/2006 | Lee et al. |
| 2006/0247581 A1* | 11/2006 | Pedersen et al. ............ 604/218 |
| 2006/0293694 A1 | 12/2006 | Futamura |
| 2007/0005135 A1 | 1/2007 | Makker et al. |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0161049 A1 | 6/2010 | Inoue |
| 2010/0185206 A1 | 7/2010 | Ichinohe et al. |
| 2010/0217273 A1* | 8/2010 | Someya et al. .............. 606/107 |
| 2010/0286704 A1 | 11/2010 | Ichinohe et al. |
| 2010/0331808 A1* | 12/2010 | Py et al. .................. 604/500 |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0018460 A1 | 1/2013 | Anderson |
| 2013/0226193 A1 | 8/2013 | Kudo et al. |
| 2013/0245635 A1 | 9/2013 | Inoue |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |

FOREIGN PATENT DOCUMENTS

| | | |
|---|---|---|
| EP | 0363213 | 4/1990 |
| EP | 1332731 | 8/2003 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |

(56) References Cited

FOREIGN PATENT DOCUMENTS

| JP | 2008-212689 A | 9/2008 |
|---|---|---|
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011155636 A1 | 12/2011 |

OTHER PUBLICATIONS

EPO Supp. Search Report dated Nov. 4, 2013 in corresponding EPO App. Ser. No. 11 766 042.3.

* cited by examiner

OCULAR IMPLANT INSERTION APPARATUS AND METHODS

TECHNICAL FIELD

The present inventions relate generally to apparatus and methods for inserting an ocular implant into an eye.

BACKGROUND

There are a variety of instances where an ocular implant is inserted into the anterior chamber, posterior chamber, cornea, vitreous space and/or other portion of an eye. Exemplary ocular implants include, but are not limited to, lenses, capsular tension rings, ocular prosthesis and lamellar transplants. An intraocular lens (IOL), for example, may be inserted into an aphakic eye that has undergone a cataract surgery or may be inserted into a phakic eye during a refractive surgery. One type of lens is a foldable lens. Foldable lenses are formed from soft material such as silicone, soft acrylic, or hydrogel and may inserted into the eye through a small incision. Lens insertion apparatus, which may be used to push a foldable lens into an eye through a small diameter insertion tube, generally include push-type apparatus and screw-type apparatus. In both cases, the lens insertion apparatus may include a plunger with a rod that is used to push the lens through the insertion tube, and an operational portion that is used to drive the rod.

During use of push-type lens insertion apparatus, the operator presses the operational portion against a resistance, such as the friction between the lens and the inner wall of insertion tube, to move the rod and lens through the insertion tube. One example of such an apparatus is disclosed in Japanese Unexamined Pat. App. Pub. No. 2000-516487 (also published as U.S. Pat. No. 5,766,181). Although such push-type apparatus are advantageous in that they may be operated with one hand, precise control of the lens movement through the insertion tube can be difficult to achieve because the pressure applied to the operational portion by the operator must be balanced against frictional resistance. This can be problematic because folded lenses, which are under a large load as they are compressed through the insertion tube, especially in those instances where the optical portion of the lens is thick or the insertion tube has a relatively small inner diameter, spring back to their unstressed shape as they exit the insertion tube. Unexpected release of the lens into the eye can, therefore, result in damage to ocular tissue. Some push-type lens insertion apparatus, such as that disclosed in Japanese Unexamined Pat. App. Pub. No. H11-510711 (also published as PCT Pub. No. WO 96/37152), are configured such that the resistance increases as the lens is pushed distally.

In screw-type lens insertion apparatus, threads are used to connect the operational portion to the main body. Rotation of the operational portion results in linear movement of the plunger rod and lens in the distal (or "lens advancing") direction. With such apparatus, one example of which is disclosed in Japanese Unexamined Pat. App. Pub. No. H11-506357 (also published as. PCT Pub. No. WO 96/28122), the travel distance of the plunger rod can be easily controlled, thereby preventing the unexpected release of the lens into the eye. Screw-type lens insertion apparatus are, however, more difficult to operate than push-type lens insertion apparatus because operation of the screw-type lens insertion apparatus requires two hands. Screw-type lens insertion apparatus are also structurally more complicated.

Attempts have also been made to harness the advantages of the push and screw-type lens apparatus, while avoiding the disadvantages, in a single apparatus. In the apparatus disclosed in Japanese Unexamined Patent Application Publication No. H5-103809, for example, a rotating mechanism may be used to control the travel distance of the plunger in a push-type apparatus. The ability of the apparatus to switch from push-type operation to screw-type operation is, however, dependent upon the behavior of the lens within the nozzle and may not be available at the time desired. Although the screw-type lens insertion apparatus disclosed in Japanese Unexamined Patent Application Publication No. 2003-210498 (also published as U.S. Pat. No. 6,666,871) may be operated with both hands, or with only one hand, the operational portion or its component for moving the plunger forward must be carefully operated to prevent unintended rotation. The operational portion also rotates as it is pushed distally, which the present inventor has determined is both distracting and unnecessary.

Accordingly, the present inventor has determined while lens insertion apparatus that can provide both push-type operation and screw-type operation are desirable, those currently available are susceptible to improvement.

SUMMARY

An exemplary insertion apparatus includes a main body defining a longitudinal axis and a plunger, movable relative to the main body, including a rod portion and an operational portion rotatably mounted on the rod portion. One of the main body and the plunger operational portion includes a helical slot and at least one longitudinally extending clearance groove that intersects the helical slot and the other of the main body and the operational portion includes at least one protrusion that is sized and shaped to fit within the helical slot and within the at least one longitudinally extending clearance groove. There are a number of advantages associated with such an apparatus. For example, such an apparatus is capable of switching between push-type operation and screw-type operation when desired by the operator.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

DETAILED DESCRIPTION OF EXEMPLARY EMBODIMENTS

The following is a detailed description of the best presently known modes of carrying out the inventions. This description is not to be taken in a limiting sense, but is made merely for the purpose of illustrating the general principles of the invention. The present inventions are also applicable to a wide variety of ocular implants which, as used herein, refers to any structure, instrumentality or device that is placed into any ocular structure or region. Ophthalmic lenses, capsular tension rings, ocular prosthesis and lamellar transplants are examples of ocular implants. Although the exemplary implementations are described below in the context of intraocular lens (IOL), the present inventions are also applicable other types of ocular implants including those yet to be developed. For example, the present inventions are applicable to other types of ophthalmic lenses. Such lenses include, but are not limited to, intraocular contact lenses, phakic IOLs, and other lenses that may be inserted into the eye.

Figure 1:
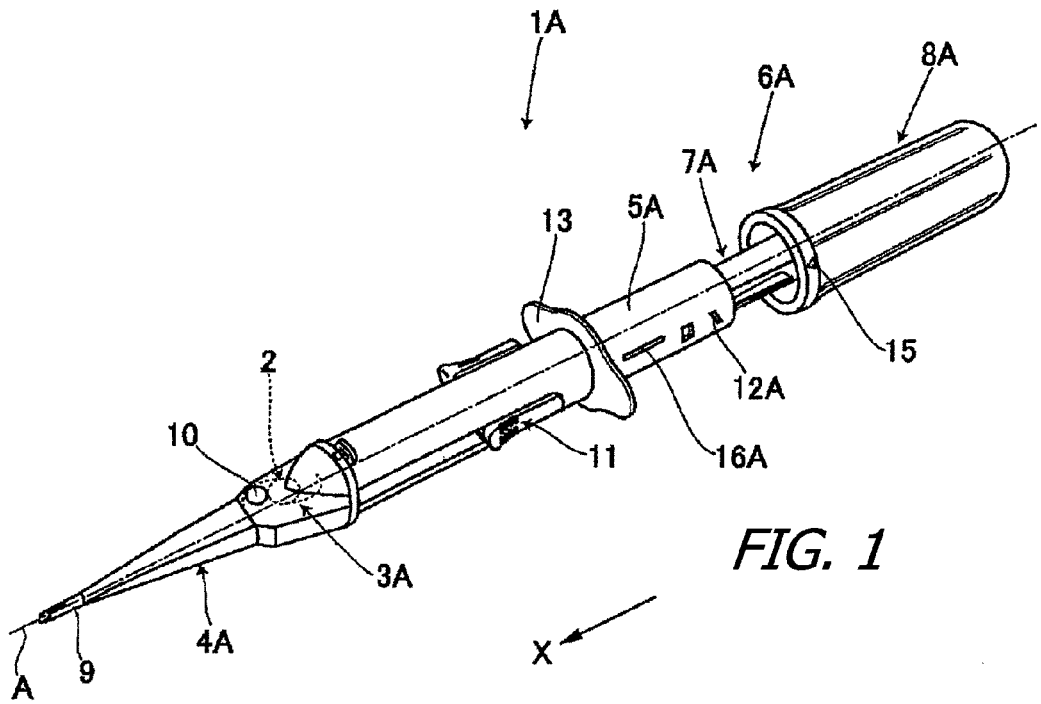
FIG. 1 is a perspective view of a lens insertion apparatus in accordance with one exemplary embodiment of a present invention.

One example of lens insertion apparatus in accordance with at least some of the present inventions is generally represented by reference numeral 1A in FIG. 1. The exemplary lens insertion apparatus 1A, may be used to insert a lens 2 (e.g., an IOL) into the eye and includes a lens placement portion 3A, a tapered insertion portion 4A, a main body 5A and a plunger 6A. The lens 2 is loaded into the lens placement portion 3A. The exemplary plunger 6A includes a rod 7A that engages the lens 2 and an operational portion 8A. The exemplary plunger 6A is also, structured such that the rod 7A may be moved in the distal direction (identified by arrow X) and the proximal direction, along axis A, through manual operation of the operational portion 8A. The tapered insertion portion 4A includes a nozzle 9 at the distal end and a through-hole 10 in communication with the lens placement portion 3A. During the insertion procedure, the lens 2 is pushed through the lens placement portion 3A, folded or otherwise compressed into a compact state in the tapered insertion portion 4A, and then released into the eye by way of the distal end of the nozzle 9. The lens 2 may be pushed by the plunger 6A, depending on the specifics of the actual implementation, through the insertion portion 4A and nozzle 9 and into the eye or, in other implementations, may be pushed over the entire range of movement from the lens placement portion 3A to the eye.

Although the present inventions are not so limited, the exemplary lens insertion apparatus 1A is a preloaded injector. The injector 1A is shipped with the lens 2 within the lens placement portion 3A.

The lens placement portion 3A in the exemplary embodiment is located at the leading end of the main body 5A. More specifically, the main body 5A is formed from a cylindrical member, and the tapered insertion portion 4A is connected to the distal end of the main body by way of the lens placement portion 3A. The exemplary insertion apparatus 1A also includes a longitudinally movable slider 11 with a lens control mechanism and a lock mechanism. The lens control mechanism (not shown) moves and deforms the lens 2 during the first stage of the insertion procedure, while the lock mechanism (not shown) prevents the plunger 6A from being moved distally until the slider 11 has been moved distally. Additional details concerning preloaded injectors that include a slider with lens control and lock mechanisms may be found in, for example, U.S. Patent Pub. No. 2010/0217273.

Figure 5:
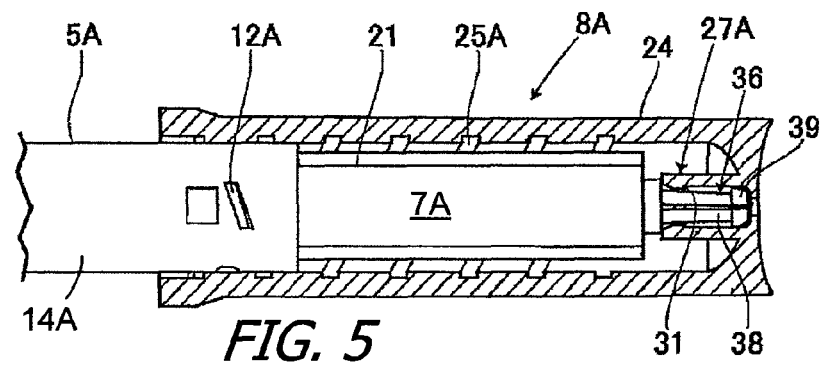
FIG. 5 is a partial section view of the proximal portion of the plunger in the exemplary lens insertion apparatus illustrated in FIG. 1.
Figure 6:
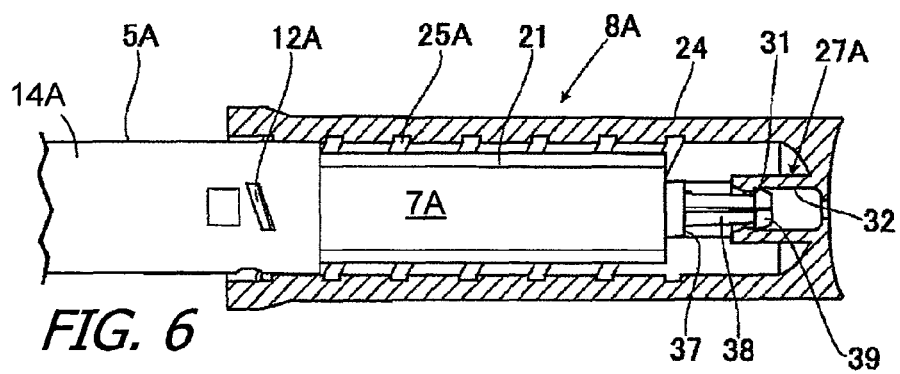
FIG. 6 is another partial section view of the proximal portion of the plunger in the exemplary lens insertion apparatus illustrated in FIG. 1.

One or more protrusions 12A may be located near the proximal end of the exemplary main body 5A. In the embodiment illustrated in FIGS. 1-7, there are two protrusions 12A (only one is visible). Referring to FIGS. 5 and 6, a first protrusion is located on one side wall 14A of the main body 5A, and oriented at an angle to axis A, and a second protrusion 12A is located on the opposite side wall 14A. The protrusions 12A define a discontinuous male screw thread (or partial screw threads) and the surfaces of the associated main body side walls 14A define the root of the screw thread(s). The protrusions 12A, which cooperate with the helical slot 25A on operational portion 8A in the manner described below, are axially offset from one another by a distance equal to one-half of the pitch of the helical slot 25A.

The exemplary insertion apparatus 1A illustrated in FIG. 1-7 also includes a hook (of "flange") portion 13 (FIG. 1) projecting outwardly from the external surface of the main body 5A. The hook portion 13, which is located in the proximal half of the main body 5A, may be used to engage fingers during push-type operation of the insertion apparatus 1A.

The insertion apparatus 1A illustrated in FIGS. 1-7 may also be provided with indicia that indicates when the relative orientation of the main body 5A and the plunger operational portion 8A is such that the operator can switch from push-type operation to screw-type operation, or from the screw-type operation to push-type operation, in the manner described below. Referring to FIG. 1, the indicia consists of a first indicia portion 15 on the operational portion 8A and a second indicia portion 16A on the main body 5A. The first indicia portion 15 is located on the external, distal end surface of the operational portion 8A. The second indicia portion 16A is provided on the external surface of the main body 5A near the proximal end. In the illustrated implementation, the first indicia portion 15 is in the form of a triangle and the second indicia portion 16A is in the form of a longitudinally extending linear mark. The functionality of the first and second indicia portions 15 and 16A is discussed below. It should also be noted that another set of first and second indicia portions 15 and 16A may be located on the opposite sides (i.e., a location offset by 180 degrees about axis A) of the main body 5A and operational portion 8A.

Figure 2:
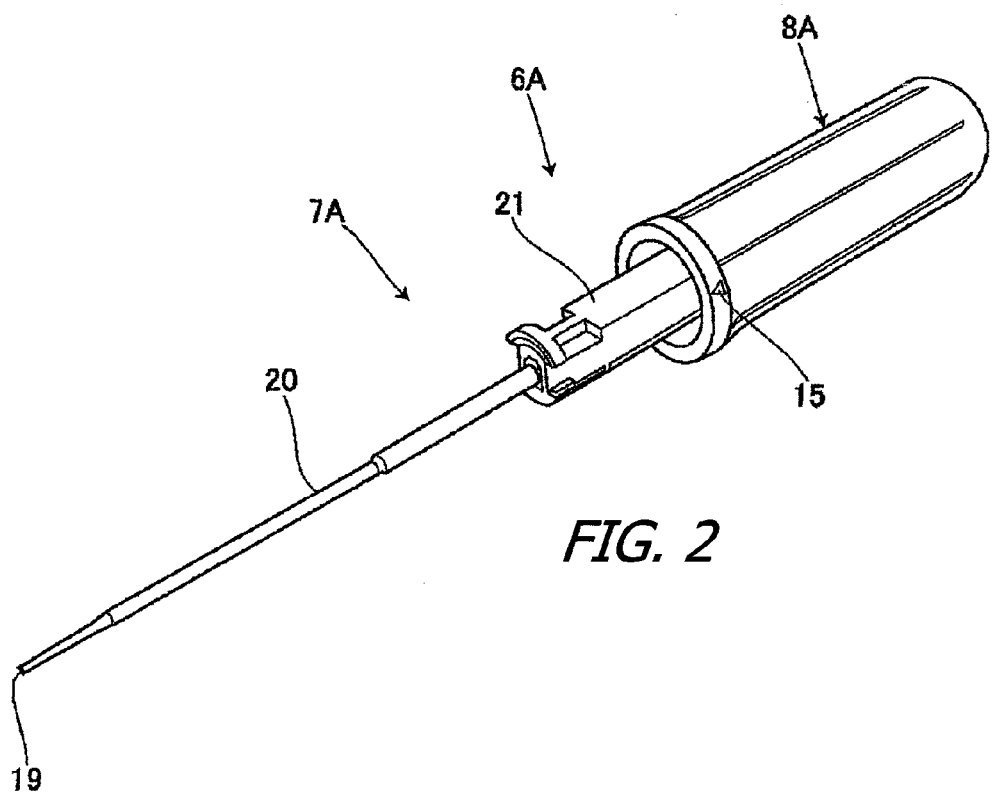
FIG. 2 is a perspective view of the plunger in the exemplary lens insertion apparatus illustrated in FIG. 1.

Turning to FIG. 2, the exemplary plunger 6A is configured such that force applied to the operational portion 8A is transmitted to the rod 7A to push the lens 2 in the distal direction. The rod 7A includes a distal rod portion 20 and a proximal rod portion 21. The distal rod portion 20 has an abutting surface 19 on its distal end that engages the outer edge of the lens 2 during the insertion procedure. The distal rod portion 20 and the proximal rod portion 21 may be integrally formed (as shown) or separate structures that are secured to one another during assembly. The operational portion 8A is axially supported on the proximal rod portion 21 of the rod 7A in such a manner that the operational portion may move axially and rotationally relative to the rod, as is described in greater detail below.

The respective configurations of the exemplary main body 5A and operational portion 8A, as well as the relationship between the two, are such that rotational movement of the operational portion results in an axial (or "longitudinal") driving force that moves the rod 7A proximally or distally depending on the direction of rotation and, in the predefined instances discussed below, force applied to the operational portion in the axial (or "longitudinal") direction drives the rod proximally or distally depending on the direction of the force.

Figure 3:
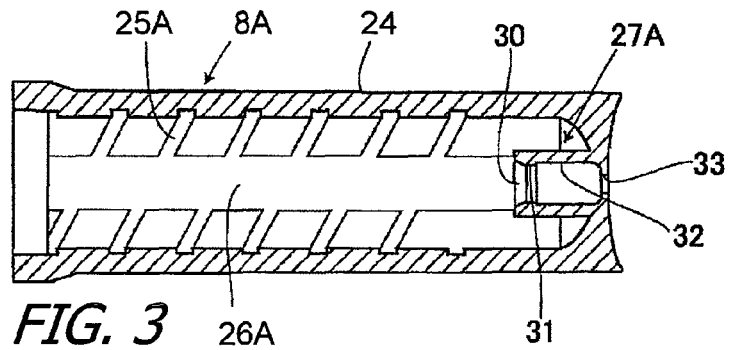
FIG. 3 is a section view of the operational portion in the exemplary lens insertion apparatus illustrated in FIG. 1.

To that end, and referring to FIG. 3, the operational portion 8A of the exemplary insertion apparatus 1A includes an operational body 24, a helical slot 25A on the inner surface of the operational body, one or more clearance grooves 26A and a bearing portion 27A. The exemplary operational body 24 has generally cylindrical shape. The distal end operational body 24 is open and the bearing portion 27A is located at the proximal end. The helical slot 25A defines a female screw thread. The respective sizes, shapes and orientations of the main body protrusions 12A and the operational body helical slot 25A are such that the helical slot may be screwed into engagement with the protrusions and, once engaged, rotation of the operational portion 8A will result in axial movement of the operational portion. The one or more clearance grooves 26A are parallel to the lens advancing axis A and, in the illustrated embodiment, extend longitudinally over at least the entire length (measured in the axial direction) of the helical slot 25A. The number of clearance grooves 26A may correspond to the number of main body protrusions 12A and, accordingly, there are two clearance grooves 26A on the internal surface of the operational body 24. The two clearance grooves 26A are identical and located on opposite sides of the operational body 24, i.e., are offset from one another by 180 degrees about the axis A, in the illustrated embodiment. The clearance grooves 26A also pass through, i.e., repeatedly intersect, the helical slot 25A. The respective sizes, shapes and orientations of the main body protrusions 12A and the operational body clearance grooves 26A are such that, when the clearance grooves and protrusions are aligned with one another, the operational portion 8A may be moved longitudinally without rotation thereof.

Figure 4:
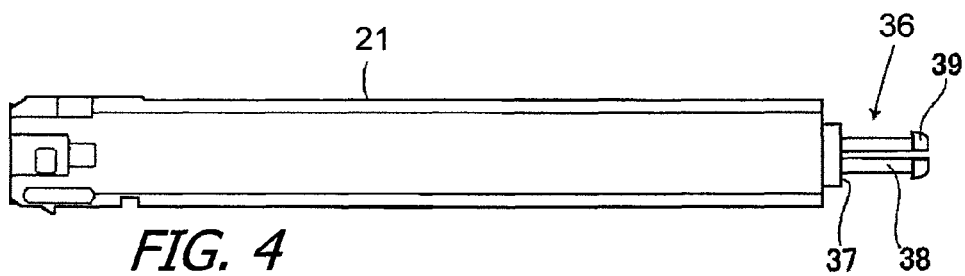
FIG. 4 is a side view of the proximal portion of the plunger rod in the exemplary lens insertion apparatus illustrated in FIG. 1.

Referring to FIGS. 3 and 4, the bearing portion 27A is configured to connect to an axial support portion 36 (discussed below) located on the proximal rod portion 21. The exemplary bearing portion 27A includes an insertion hole 30, an inwardly protruding latching portion 31, and a cylindrical lumen 32. The inwardly protruding latching portion 31 is located between the insertion hole 30 and the cylindrical lumen 32. The end of the cylindrical lumen 32 is generally closed but for an opening 33 that is smaller in diameter than the cylindrical lumen.

The axial support portion 36 is located on a proximal end surface 37 of the proximal rod portion 21 of the rod 7A. In the exemplary embodiment illustrated in FIGS. 1-7, the axial support portion 36 includes an axis portion 38 and an engaging portion 39 that extends outwardly from the proximal end of the axis portion (note FIG. 4). The length, of the axis portion 38, i.e., the distance from the proximal end surface 37 to the engaging portion 39, generally defines the axial distance over which the latching portion 31 and, therefore, the operational body 24 may move relative to the proximal rod portion 21 when the main body protrusions 12A are located within the clearance grooves 26A (note FIGS. 5 and 6).

Referring to FIGS. 4 and 5, the operational portion 8A may be mounted on the rod 7A by inserting the axial support portion 36 into the bearing portion 27A by way of the insertion hole 30. The axis portion 38 will compress as the engaging portion 39 passes the latching portion 31, and then return to its expanded state, thereby preventing removal of the axial support portion 36 from the bearing portion 27A. As illustrated in FIGS. 5 and 6, once mounted onto the axial support portion 36 of the rod 7A, the operational portion 8A is axially movable along the axis portion 38 in the proximal-distal direction over a range defined by the proximal end surface 37 and the engaging portion 39, and is also rotatable relative to the rod. The cylindrical body 32 of the operational body 24 is sized to accommodate such movement of the operational portion 8A. Additionally, as the diameter of the opening 33 is smaller than that of the cylindrical body 32 and engaging portion 39, the axial support portion 36 will not protrude through the end of the operational body 24.

The respective configurations of the bearing portion 27A and the axial support portion 36 are such that the operational portion 8A can be both rotated relative to the rod 7A and moved a predetermined distance axially relative to the rod. The predetermined distance may be, at a minimum, the maximum distance that the operational portion 8A must travel proximally (i.e., rearward) in the axial direction as the protrusions 12A move from the helical slot 25A to the clearance grooves 26A due to rotation of the operational portion. The distance will be a function of the pitch of the helical slot 25A as well as the numbers of protrusions 12A and clearance grooves 26A.

The protrusions 12A are located on opposite sides of the exemplary main body 5A, i.e., are offset from one another by 180 degrees about the axis A, and the clearance grooves 26A are located on opposite sides of the exemplary operational body 24, i.e., are offset from one another by 180 degrees about the axis A. As a result, one half-turn or less of the operational portion 8A is required to move the clearance grooves 26A to into alignment with the protrusions 12A. Therefore, the above-mentioned predetermined distance requires at least half of the length aspect of the pitch of the screw portion 25A.

The exemplary lens insertion apparatus 1A may be operated as follows. First, viscoelastic material is supplied to the lens placement portion 3A, which is preloaded with a lens 2 that may be stored in a generally flat, unstressed state. The slider 11 is then moved forward, which causes the lens 2 to be pushed distally out of the lens placement portion 3A and deformed into a predetermined shape. After that, the rod 7A may be moved distally through operation of the operational portion 8A. Such operation may be rotation of the operational portion 8A while the protrusions 12A are located within the helical slot 25 (i.e., screw-type), or may be pushing the operational portion distally when the protrusions are located within the clearance grooves 26A (i.e., push-type).

With respect to screw-type operation of the operational portion 8A, the operational portion is moved distally until the proximal end of the helical slot 25 abuts the protrusions 12A. At this point, the abutting surface 19 of rod 7A does not abut the outer edge of the lens 2. The operational portion 8A may then be rotated clockwise to engage the protrusions 12A with the helical slot 25, and subsequent rotation will be translated into axial movement of the operational portion and rod 7A. The distance that the operational portion 8A and rod 7A will move axially is a function of the pitch of the helical slot 25A and the amount of rotation. The rod 7A will then engage the lens 2 and drive the lens through the inside of the tapered insertion portion 4A, thereby further compressing the lens, as rotation of the operational portion 8A continues. Screw-type operation may continue, if push-type operation is not desired, until the rod 7A pushes the lens 2 through the nozzle and into the eye.

Turning to push-type operation, and as noted above, push-type operation may proceed when the protrusions 12A are located within the clearance grooves 26A. The user may align the clearance grooves 26A with the protrusions 12A, and proceed with push-type operation, immediately after the slider 11 has been moved forward or after some degree of screw-type operation has taken place. In order to switch from screw-type operation to push-type operation, the orientation of the operational portion 8A relative to the main body 5A must be such that the clearance grooves 26A are aligned with the protrusions 12A. This may be accomplished by rotating the operational portion 8A counterclockwise or clockwise, although counterclockwise is preferred because counterclockwise rotation will not result in additional distal advancement of the lens and, as discussed below, will not result in axial movement of the rod 7A in the proximal direction. Once the clearance grooves 26A are aligned with the protrusions 12A, the operational portion 8A (and rod 7A) may be advanced distally without rotation of the operational portion by simply applying a pushing force to the operational portion. The operation portion 8A will not rotate on its own. Also, the user will not be able to rotate the operation portion 8A when the protrusions 12A are between slot-clearance groove intersections. The pushing force may be applied, and the rod 7A moved forwardly, until the lens 2 enters the eye through the distal end of the nozzle 9, or until the user desires to switch to screw-type operation.

The clearance grooves 26A also prevent rotation of the operational portion 8A unless and until the protrusions 12A are aligned with a portion of the helical slot 25A and the operator demonstrates the intent to switch to screw-type operation, precisely when there is such alignment, by applying rotational force to the operational portion. Absent the application of rotational force to the operational portion 8A when the protrusions 12A are aligned with a portion of the helical slot 25A, the clearance grooves 26A will guide the protrusions 12A (and operational portion 8A) in the axial direction and the operational portion will not rotate.

It should also be noted here that, as discussed above and illustrated in FIGS. 5 and 6, the respective configurations of the bearing portion 27A and the axial support portion 36 are such that the operational portion 8A may be moved a predetermined distance in the proximal direction without moving the rod 7A. The predetermined distance is sufficient to accommodate the amount of rotation necessary to align the clearance grooves 26A with the protrusions 12A (i.e., one-half rotation or less in the embodiment illustrated in FIGS. 1-7). As such, contact between the rod 7A and the lens 2 may be maintained while the user switches from screw-type operation to push-type operation. Additionally, as the exemplary clearance grooves 26A are formed parallel to the lens advancing axis A over the entire length of the helical slot 25A, it is possible to switch from screw-type operation to push-type operation, or from push-type operation to screw-type operation, whenever the operator desires.

Figure 7:
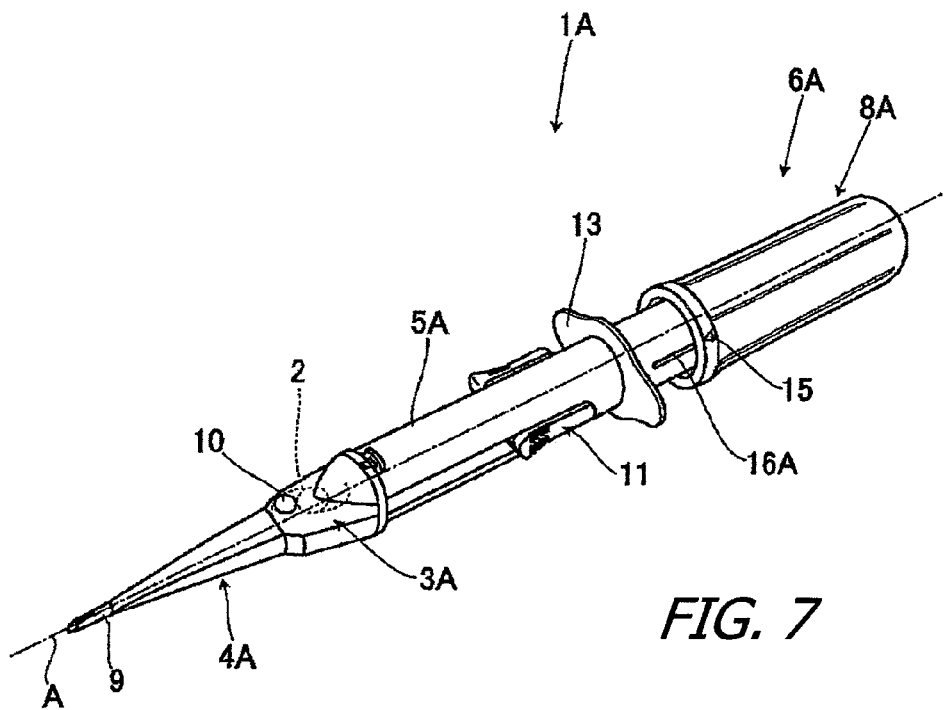
FIG. 7 is a perspective view of the exemplary lens insertion apparatus illustrated in FIG. 1 with the plunger moved distally.

The first and second indicia portions 15 and 16A indicate, when aligned with one another, that the exemplary lens insertion apparatus 1A is susceptible to push-type operation. Referring to FIG. 7, the first and second indicia portions 15 and 16A are located on the main body 5A and the operational portion 8A such that the clearance grooves 26A are aligned with the protrusions 12A when the first and second indicia portions are aligned with one another. In other words, when the user desires to employ push-type operation, the user need only rotate the operational portion 8A (if necessary) until first and second indicia portions 15 and 16A are aligned. The length and location of the exemplary second indicia portion 16A insures that it will be visible regardless of the position of the operational portion 8A.

Figure 8:
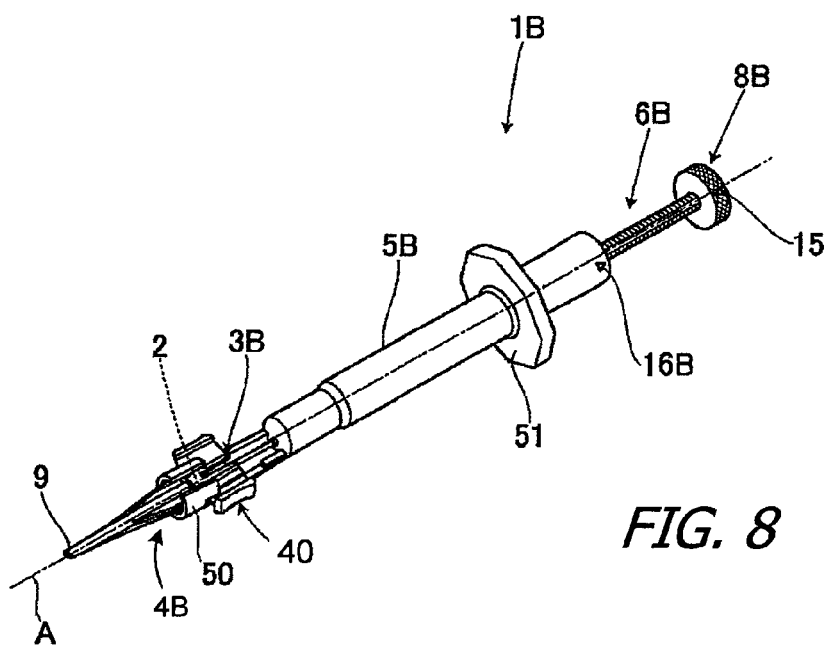
FIG. 8 is a perspective view of a lens insertion apparatus in accordance with one exemplary embodiment of a present invention.

Another exemplary lens insertion apparatus is generally represented by reference numeral 1B in FIG. 8. Insertion apparatus 1B is similar to insertion apparatus 1A in many respects and similar elements are represented by similar reference numerals. For example, the insertion apparatus 1B includes a main body 5B with a hook portion 51, and a plunger 6B (FIG. 10) with a rod 7B and an operational portion 8B. Here, however, the insertion apparatus 1B is a cartridge-based insertion apparatus instead of a preloaded insertion apparatus. To that end, an exemplary cartridge 40 includes a lens placement portion 3B, a tapered insertion portion 4B and a nozzle 9. A lens 2 (e.g., an IOL) may be folded and loaded into the cartridge 40, and the cartridge then secured to an attachment portion 50 located near the distal end of the main body 5B, at the time of the insertion procedure. The plunger 6B pushes the lens 2 from the lens placement portion, through the tapered insertion portion where it is further compressed, and then into the eye by way of the nozzle 9. The cartridge 40 may be removed from the attachment portion 50 after the procedure.

Figure 9:
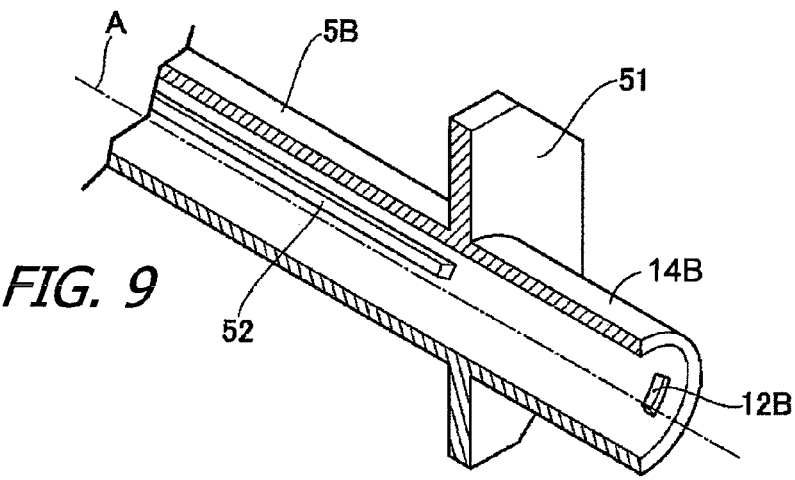
FIG. 9 is a perspective section view of the main body in the exemplary lens insertion apparatus illustrated in FIG. 8.

Turning to FIG. 9, the inner surface of the exemplary main body includes one or more protrusions 12B and one or more ribs 52. There are two protrusions 12B, located 180 degrees apart, on the inner surfaces of the main body side walls 14B in the illustrated implementation. The protrusions 12B define a partial female screw thread and the surfaces of the associated main body side walls 14B define the root of the screw thread. The protrusions 12B cooperate with the operational portion 8B in the same manner as the protrusions and operational portion described above. There are also two ribs 52, located 180 degrees apart, on the inner surfaces of the main body side walls 14B in the illustrated implementation. The longitudinal orientation of the ribs 52 in the illustrated embodiment is parallel to the lens advancing axis A. The ribs 52 prevent rotation of the rod 7B, as discussed below, while allowing the rod to move parallel to the lens advancing axis A.

Figure 10:
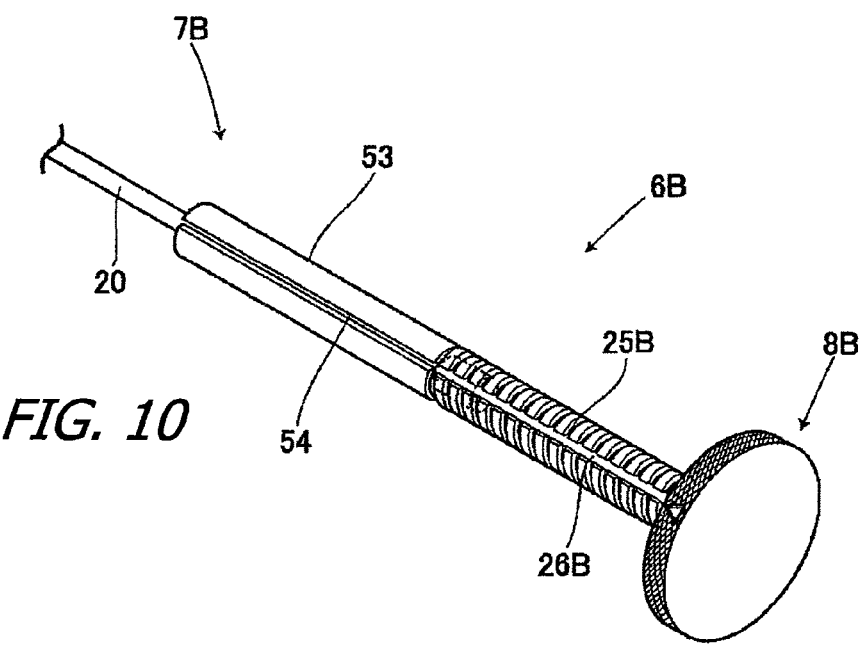
FIG. 10 is a perspective view of the plunger in the exemplary lens insertion apparatus illustrated in FIG. 8.
Figure 11:
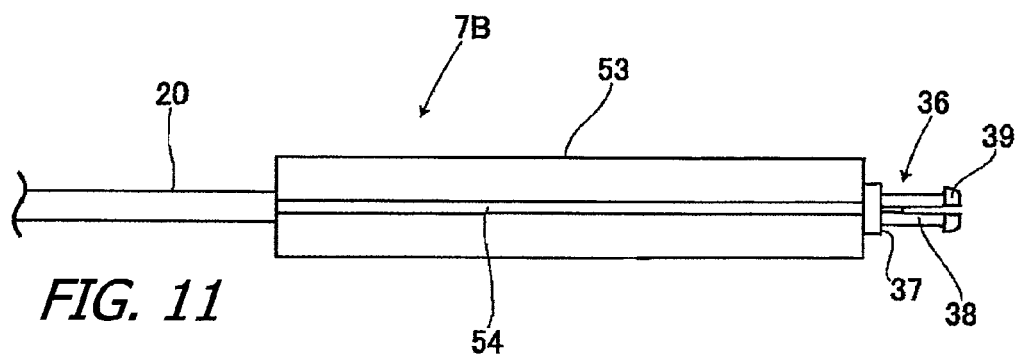
FIG. 11 is a side view of the proximal portion of the plunger rod in the exemplary lens insertion apparatus illustrated in FIG. 8.

As illustrated in FIGS. 10 and 11, the exemplary plunger rod 7B includes a distal rod portion 20 and a proximal rod portion 53. One or more guide grooves 54, in which the one or more ribs 52 reside, are located on the exterior of the proximal rod portion 53. There are two guide grooves 54, located 180 degrees apart, on the inner surfaces of the main body side walls 14B in the illustrated implementation. The interaction between the ribs 52 and grooves 54 prevents the rod 7B from rotating, while allowing the rod to move axially in the proximal and distal directions. An axial support portion 36 is located on the proximal end of the proximal rod portion 53.

Figure 12:
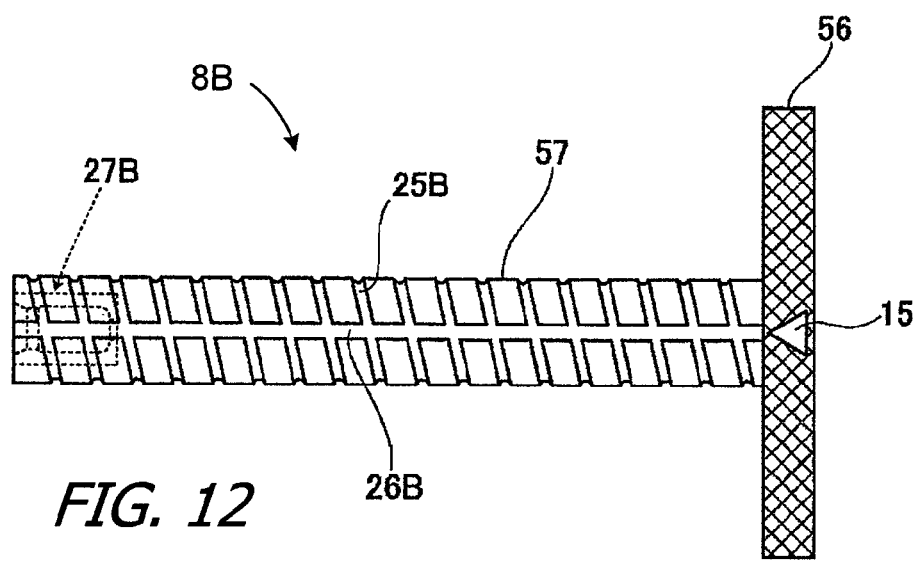
FIG. 12 is a side view of the operational portion in the exemplary lens insertion apparatus illustrated in FIG. 8.

Referring to FIG. 12, the exemplary operational portion 8B includes a disk-shaped operational body 56 and a rod-shaped body 57. The operational body 56 and rod-shaped body 57 may be integrally formed (as shown), or may be separate structures that are secured to one another. The outer diameter of the rod-shaped body 57 is substantially the same as that of the proximal rod portion 53 (FIGS. 10 and 11). A helical slot 25B and one or more clearance grooves 26B are formed in the outer surface of the rod-shaped body 57, and a bearing portion 27B is located at the distal end of the rod-shaped body. The helical slot 25B defines a female screw thread and the respective sizes, shapes and orientations of the protrusions 12B and the helical slot 25B are such that the helical slot may be screwed into engagement with the protrusions and, once engaged, rotation of the operational portion 8B will result in axial movement plunger 6B. The one or more clearance grooves 26B are parallel to the lens advancing axis A and, in the illustrated embodiment, extend longitudinally over at least the entire length (measured in the axial direction) of the helical slot 25B. The number of clearance grooves 26B may correspond to the number of main body protrusions 12B and, accordingly, there are two clearance grooves 26B on the external surface of the rod-shaped body 57. The clearance grooves 26B in the illustrated embodiment are located on opposite sides of the rod-shaped body 57, i.e., are offset from one another by 180 degrees about the axis A. The clearance grooves 26B also pass through, i.e., repeatedly intersect, the helical slot 25B. The respective sizes, shapes and orientations of the main body protrusions 12B and the operational body clearance grooves 26B are such that, when the clearance grooves and protrusions are aligned with one another, the operational portion 8B may be moved longitudinally, without rotation thereof.

The exemplary bearing portion 27B includes the insertion hole 30, latching portion 31, and cylindrical body 32 described above. The bearing portion 27B (FIG. 12) and axial support portion 36 (FIG. 11) operate in the manner describe above with reference to FIGS. 5 and 6 to facilitate axial movement of the operational portion 8B relative to the rod 7B. Such axial movement, in turn, facilitates switching from screw-type operation to push-type operation, or from push-type operation to screw-type operation, whenever the operator desires, as is also described above. To that end, and referring to FIG. 8, the exemplary insertion apparatus 1B is provided with first and second indicia 15 and 16B on the main body 5B and operational portion 8B that may be used to align the main body protrusions 12B and clearance grooves 26B in the manner also described above. Another set of first and second indicia portions 15 and 16B may be located on the opposite sides (i.e., locations offset by 180 degrees about axis A) of the main body 5B and operational portion 8B in some implementations. Alternatively, because the clearance grooves 26B are visible during use and can be aligned with the second indicia 16B, the first display portion may be omitted.

Figure 13:
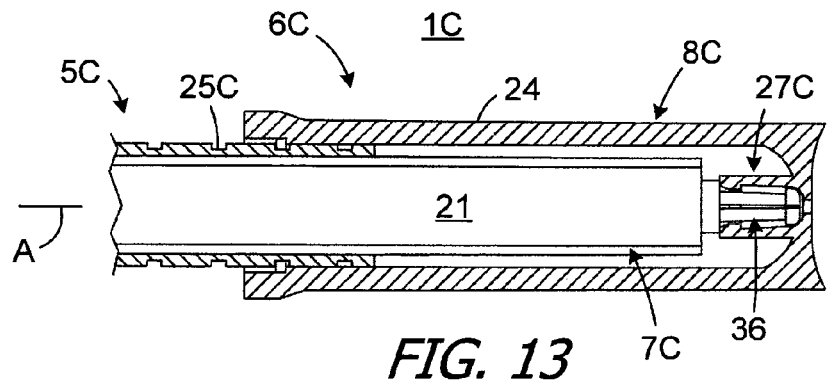
FIG. 13 is a partial section view of a lens insertion apparatus in accordance with one exemplary embodiment of a present invention.
Figure 14:
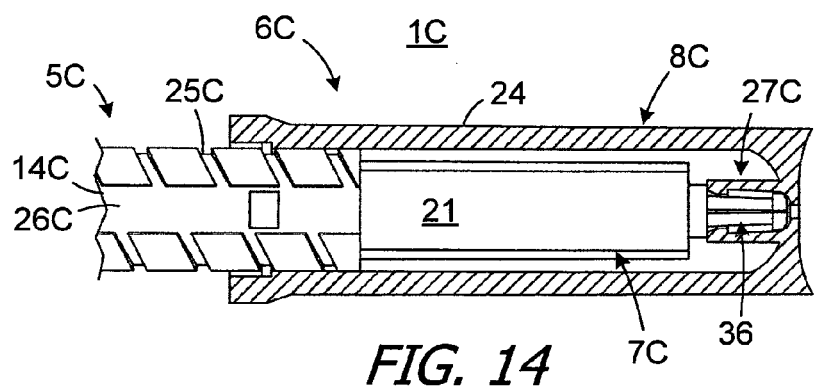
FIG. 14 is another partial section view of the exemplary lens insertion apparatus illustrated in FIG. 13.
Figure 15:
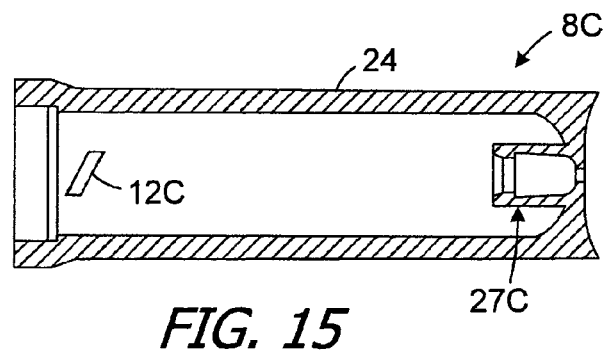
FIG. 15 is a section view of the operational portion of the exemplary lens insertion apparatus illustrated in FIG. 13.

Turning to FIGS. 13-15, a lens insertion apparatus that, for example, is otherwise identical to the lens insertion apparatus 1A illustrated in FIGS. 1-7 in form and operation may be configured such that the locations of the one or more protrusions, the one or more clearance grooves, and the helical slot are reversed. The exemplary lens insertion apparatus 1C illustrated in FIG. 13-15 includes, for example, a main body 5C and a plunger 6C. The plunger 6C includes a rod 7C and an operational portion 8C. The rod 7C includes a distal rod portion (not shown), a proximal rod portion 21 and an axial support portion 36. The operational portion 8C includes an operational body 24 and a bearing portion 27C. The insertion apparatus 1C also includes a lens placement portion, tapered insertion portion, and nozzle, which are not shown.

Here, however, the operational portion 8C includes one or more protrusions 12C. There are two protrusions 12C, located 180 degrees apart on the inner surface of the operational body 24, in the illustrated implementation. The protrusions 12C define a partial male screw thread and the inner surface of the operational body 24 defines the root of the screw thread. A helical slot 25C and one or more clearance grooves 26C are formed on the outer surface of the main body 5C. The helical slot 25C defines a female screw thread and the respective sizes, shapes and orientations of the protrusions 12C and the helical slot are such that the protrusions may be screwed into engagement with the helical slot and, once engaged, rotation of the operational portion 8C will result in axial movement plunger 6C. The one or more clearance grooves 26C are parallel to the lens advancing axis A and, in the illustrated embodiment, extend longitudinally over at least the entire length (measured in the axial direction) of the helical slot 25C. The number of clearance grooves 26C may correspond to the number of main body protrusions 12C and, accordingly, there are two clearance grooves 26C on the external surface of the main body 5C. The clearance grooves 26C in the illustrated embodiment are located on opposite sides of the main body 5C, i.e., are offset from one another by 180 degrees about the axis A. The clearance grooves 26C also pass through, i.e., repeatedly intersect, the helical slot 25C. The respective sizes, shapes and orientations of the operational portion protrusions 12C and the main body clearance grooves 26C are such that, when the clearance grooves and protrusions are aligned with one another, the operational portion 8C may be moved longitudinally without rotation thereof.

Figure 16:
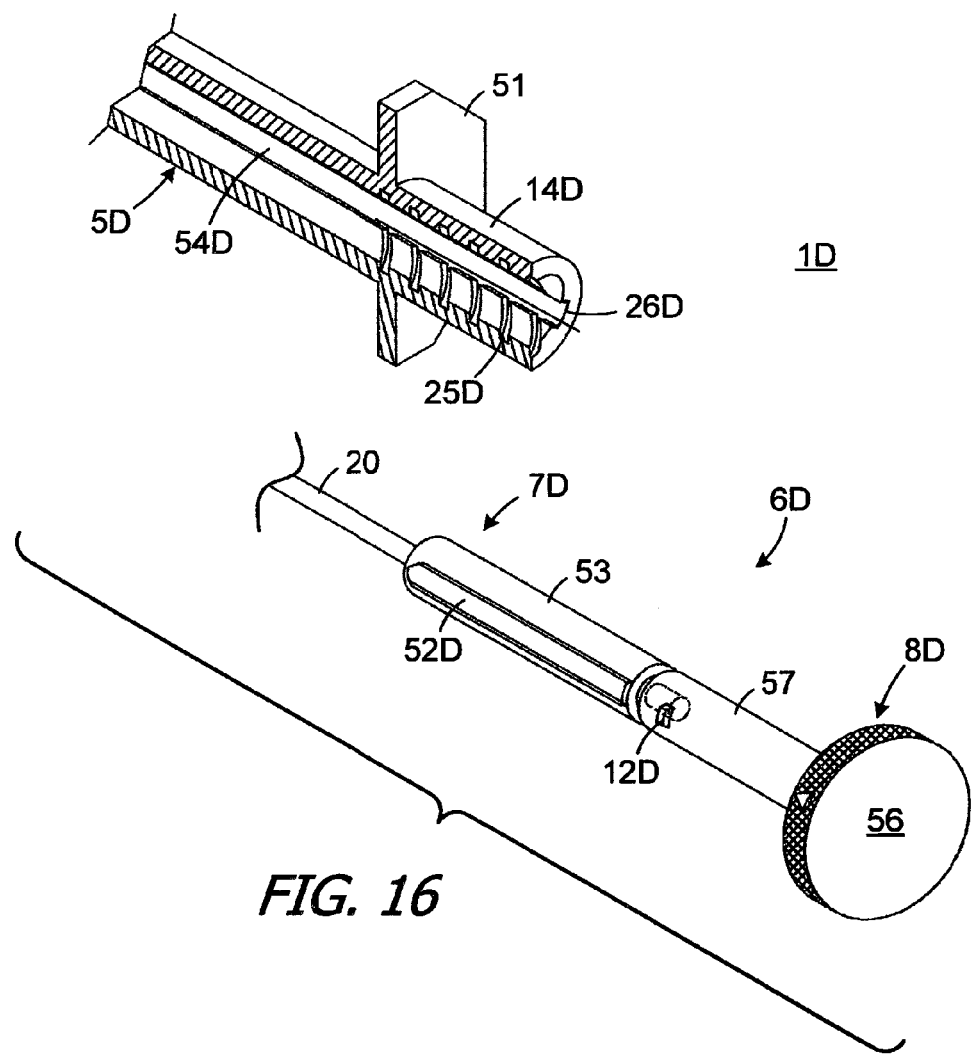
FIG. 16 is an exploded, perspective, partial section view of a lens insertion apparatus in accordance with one exemplary embodiment of a present invention.
Figure 17:
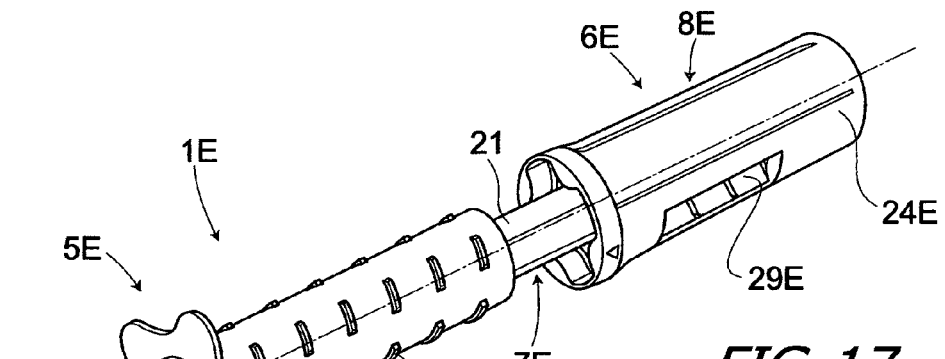
FIG. 17 is a perspective view of a lens insertion apparatus in accordance with one exemplary embodiment of a present invention.
Figure 18:
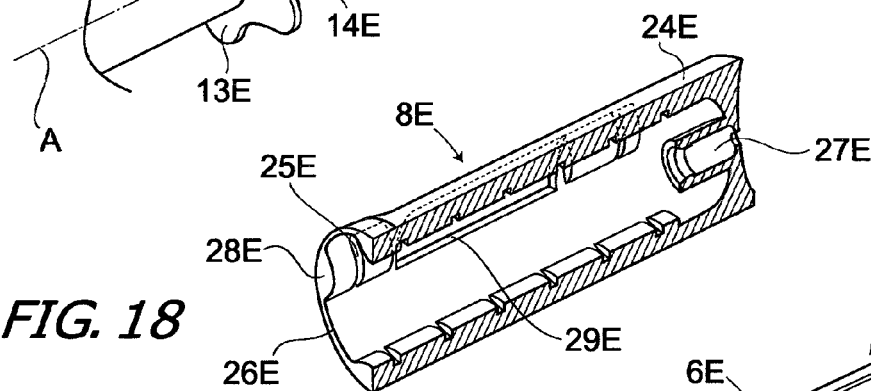
FIG. 18 is a perspective section view of the operational portion of the exemplary lens insertion apparatus illustrated in FIG. 17.
Figure 19:
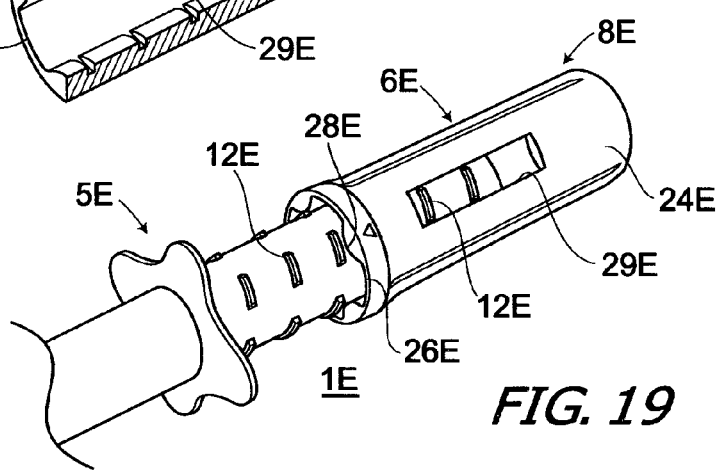
FIG. 19 is a perspective view of the exemplary lens insertion apparatus illustrated in FIG. 17 with the operational portion oriented for screw-type operation.

Another exemplary lens insertion apparatus is generally represented by reference numeral 1D in FIG. 16. Lens insertion apparatus 1D is substantially similar in form and operation to the lens insertion apparatus 1B illustrated in FIGS. 8-12 and similar elements are represented by similar reference numerals. For example, the insertion apparatus 1D is cartridge-based and includes a main body 5D with a hook portion 51, and a plunger 6D with a rod 7D and an operational portion 8D. Here, however, the inner surface of the exemplary main body 5D includes a helical slot 25D, one or more clearance grooves 26D, and one or more guide grooves 54D. The clearance and guide grooves 26D and 54D may be combined into single grooves (as shown) or may be separate grooves. With respect to the plunger 6D, the rod 7D includes a distal rod portion 20 and a proximal rod portion 53 with one or more ribs 52D that reside in the guide groves 54D. The operational portion 8D has a disk-shaped operational body 56 and a rod-shaped body 57 that may be connected to one another in the manner described above (i.e., with a bearing portion and axial support portion). One or more protrusions 12D are carried on the outer surface of the rod-shaped body. The operational body 56 and rod-shaped body 57 may be integrally formed (as shown), or may be separate structures that are secured to one another.

In the illustrated embodiment, there are two ribs (or "rails" or "mechanical keys") 52D, located 180 degrees apart, and there are two guide grooves 54D, also located 180 degrees apart, that together prevent rotation of the rod 7D while allowing the rod to move parallel to the lens advancing axis A. There are also two protrusions 12D, located 180 degrees apart. The protrusions 12D define a partial male screw thread and the surface of the rod-shaped body 57 defines the root of the screw thread. The helical slot 25D defines a female screw thread and the respective sizes, shapes and orientations of the protrusions 12D and the helical slot 25D are such that the protrusions may be screwed into engagement with the helical slot and, once engaged, rotation of the operational portion 8D will result in axial movement plunger 6D. The one or more clearance grooves 26D are parallel to the lens advancing axis A and, in the illustrated embodiment, extend longitudinally over at least the entire length (measured in the axial direction) of the helical slot 25D. There are two clearance grooves 26D, offset from one another by 180 degrees, in the illustrated embodiment. The clearance grooves 26D also pass through, i.e., repeatedly intersect, the helical slot 25D. The respective sizes, shapes and orientations of the main body protrusions 12D and the clearance grooves 26D are such that, when the clearance grooves and protrusions are aligned with one another, the operational portion 8D may be moved longitudinally without rotation thereof.

The embodiments illustrated in FIGS. 1-16 each include two protrusions that are 180 degrees apart and two clearance grooves that are 180 degrees apart. The present inventions are not, however, so limited. For example, there may be one, three, four or more of each. For example, there may be four spaced protrusions, offset by 90 degrees, which follow the pitch of the associated helical slot.

Turning to FIGS. 17-20, the exemplary lens insertion apparatus 1E illustrated therein is substantially similar to the insertion apparatus 1A described above with reference to FIGS. 1-7 in form and operation. With respect to the similarities, the insertion apparatus 1E includes, among other things, a main body 5E and a plunger 6E with a rod 7E and an operational portion 8E. The main body 5E has a hook portion 13E, an annular wall 14E and a plurality of protrusions 12E. There is also a lens placement portion, a tapered insertion portion, and a nozzle, which are not shown. The rod 7E has a distal rod portion (not shown) and a proximal rod portion 21. The operational portion 8E has an operational body 24E, a helical slot 25E, clearance grooves 26E and a bearing portion 27E that is connected to an axial support portion as is described above.

Figure 20:
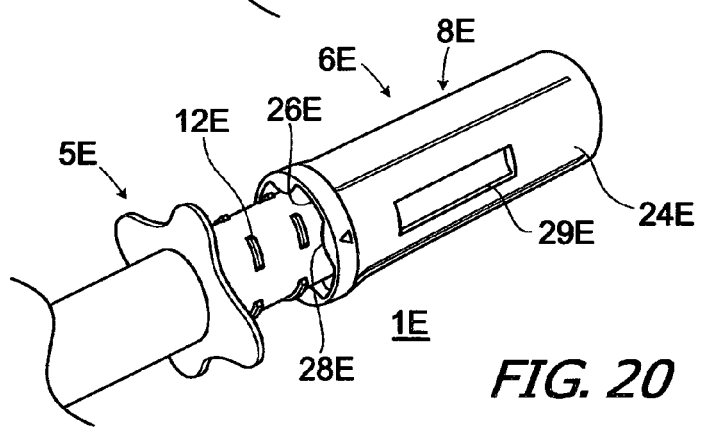
FIG. 20 is a perspective view of the exemplary lens insertion apparatus illustrated in FIG. 17 with the operational portion oriented for push-type operation.

Turning to the differences between lens insertion apparatus 1A and lens insertion apparatus 1E, lens insertion apparatus 1E has a plurality of protrusions 12E that are spaced circumferentially and axially on the main body 5E. The protrusions define a male screw thread. The protrusions 12E are aligned in four linear rows in the axially direction, which are parallel to axis A, and adjacent rows are circumferentially offset by 90 degrees. The inner surface of the operational portion 8E has four clearance grooves 26E that are separated by axially extending protrusions 28E. During screw-type operation of the lens operational portion 8E, rotation of the operational portion while the protrusions 12E are in the helical slot 25E is translated into axial movement of the operational portion and rod 7E. The user may switch to push-type operation by aligning the clearance grooves 26E with the rows of protrusions 12E. To that end, the operational portion 8E also has a window 29E, which is aligned with one of the protrusions 28E, that allows the user to determine whether the clearance grooves 26E and the rows of protrusions 12E are aligned. In the orientation illustrated in the FIG. 19, for example, the main body protrusions 12E are aligned with the operational portion protrusions 28E, thereby limiting operation to screw-type operation, and some of the main body protrusions are visible the window 29E. It should also be noted that the window 29E makes it easier to grip the operational portion 8E during screw-type operation. Conversely, the orientation illustrated in FIG. 20 is 90 degrees offset from the orientation illustrated in FIG. 19. Here, the four clearance grooves 26E are aligned with the four rows of protrusions 12E, thereby enabling push-type operation, and no protrusions 12E are visible through the window 29E.

Figure 21:
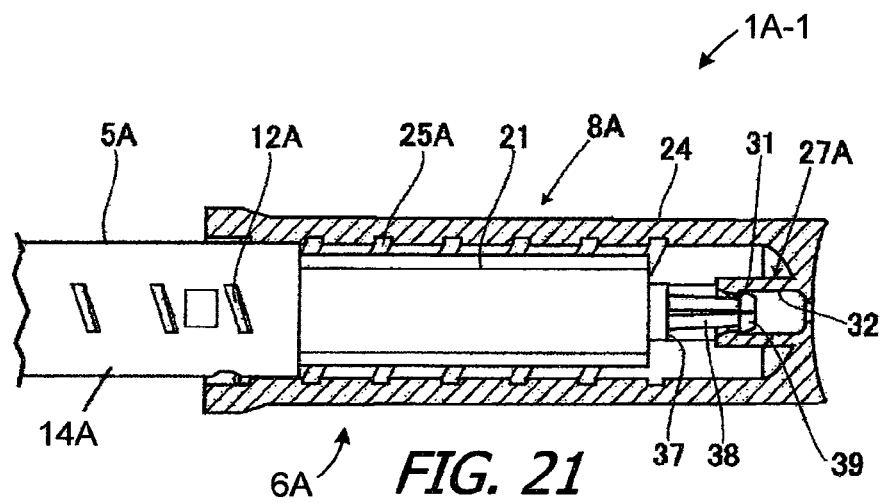
FIG. 21 is a partial section view of a lens insertion apparatus in accordance with one exemplary embodiment of a present invention.

Yet another exemplary lens insertion apparatus is generally represented by reference numeral 1A-1 in FIG. 21. Insertion apparatus 1A-1 is essentially identical to the insertion apparatus 1A described above with reference to FIGS. 1-7. Here, however, there is a plurality of axially spaced protrusions 12A on one or both sides of the main body 5A. The spacing is equal to the pitch of the associated helical groove 25A. One advantage of the use of rows of multiple axially spaced protrusions 12A, both here and the apparatus illustrated in FIGS. 17-20, is that it increases the stability of the movement of the operational portions during screw-type and push-type operation.

Figure 22:
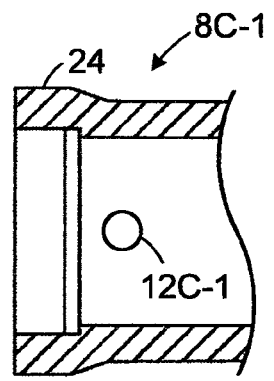
FIG. 22 is a section view of an operational portion in accordance with one exemplary embodiment of a present invention.
Figure 23:
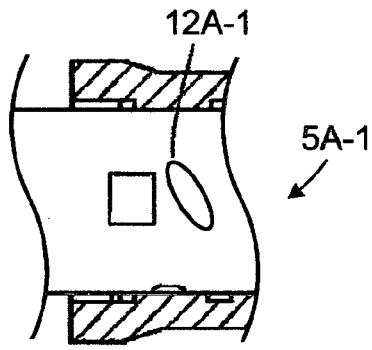
FIG. 23 is a partial section view of a main body and an operational portion in accordance with one exemplary embodiment of a present invention.
Figure 24:
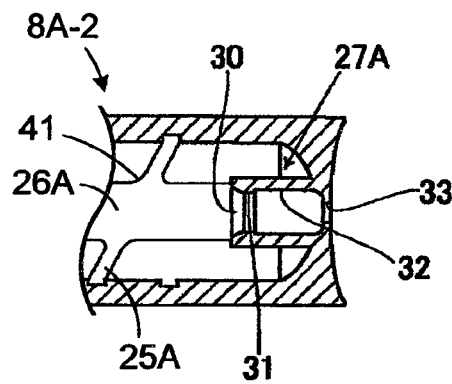
FIG. 24 is a section view of an operational portion in accordance with one exemplary embodiment of a present invention.

The exemplary protrusions discussed above have shapes corresponding to a portion of a screw thread. In other embodiments, which may be otherwise identical to any of the embodiments described above, the protrusions may be other shapes such as, for example, semispherical, elliptical or other curved shapes. By way of example, the exemplar operational portion 8C-1 illustrated in FIG. 22 includes one or more hemispherical projections 12C-1 and the exemplary main body 5A-1 illustrated in FIG. 23 includes one or more semi-ellipsoidal projections 12A-1. Such curved shapes make the transition from one type of operation (e.g., screw-type) to the other (e.g., push-type) easier and less abrupt. Alternatively, or in addition, the intersections between the helical slot and the one or more clearance grooves may include curved corners in embodiments that may be otherwise identical to any of the embodiments described above. As illustrated for example in FIG. 24, operational portion 8A-2 includes curved corners 41 at the intersections of the helical slot 25A and the one or more clearances grooves 26A. Here too, the curved shape makes the transition from one type of operation to the other easier and less abrupt.

Figure 25:
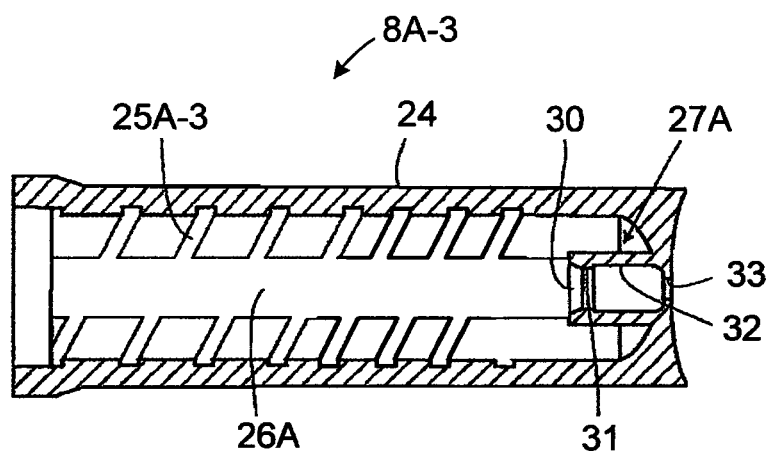
FIG. 25 is a section view of an operational portion in accordance with one exemplary embodiment of a present invention.

The present inventions are not limited to the exemplary embodiments described above. By way of example, but not limitation, the number of protrusions (or rows of protrusions) may or may not be equal to the number of the clearance grooves. The number of clearance grooves may be greater than the number of protrusions in those instances where the numbers are not equal. Also, although the pitches of the helical slots are constant in the embodiments described above, the pitches may vary along the axial length of the slots. The pitch of the slot may be smaller near the proximal end of the operational portion, for example, so that operational portion controls the travel distance of the lens more accurately as the lens is passing through the distal end of the insertion portions. For example, the operational portion 8A-3 in FIG. 25 includes a helical slot 25A-3 with a pitch that is smaller near the proximal end of the operational portion. The orientation of the helical slots may also be reversed so that counterclockwise rotation of the results in distal movement of the operational portion.

Numerous other modifications and/or additions to the above-described preferred embodiments would be readily apparent to one skilled in the art. It is intended that the scope of the present inventions extends to all such modifications and/or additions.

The invention claimed is:

1. An ocular implant insertion apparatus, comprising:
a main body defining a longitudinal axis;
a plunger, movable relative to the main body, including a rod portion and an operational portion rotatably mounted on the rod portion;
wherein
one of the main body and the operational portion includes a helical slot and at least one longitudinally extending clearance groove that repeatedly intersects the helical slot;
the other of the main body and the operational portion includes a protrusion that is sized and shaped to fit within the helical slot such that the protrusion will remain within the helical slot during rotation of the helical slot relative to the protrusion and is sized and shaped to fit within the at least one longitudinally extending clearance groove such that the protrusion will remain within the at least one longitudinally extending clearance groove during longitudinal movement of the at least one longitudinally extending clearance groove relative to the protrusion; and
the respective configurations of the helical slot, the at least one longitudinally extending clearance groove and the protrusion are such that the protrusion can move from the helical slot to the at least one longitudinally extending clearance groove and from the at least one longitudinally extending clearance groove to the helical slot.

2. An ocular implant insertion apparatus as claimed in claim 1, further comprising:
an implant placement portion associated with the main body and configured to hold an ocular implant.

3. An ocular implant insertion apparatus as claimed in claim 2, wherein the implant placement portion is permanently secured to the main body.

4. An ocular implant insertion apparatus as claimed in claim 2, wherein the Implant placement portion comprises a cartridge.

5. An ocular implant insertion apparatus as claimed in claim 1, wherein the operational portion is mounted on the rod portion such that the operational portion is longitudinally movable a predetermined distance relative to the rod portion.

6. An ocular implant insertion apparatus as claimed in claim 5, wherein the predetermined distance is equal to a pitch of the helical slot.

7. An ocular implant insertion apparatus as claimed in claim 1, wherein
the at least one longitudinally extending clearance groove comprises first and second clearance grooves; and
the protrusion comprises first and second protrusions.

8. An ocular implant insertion apparatus as claimed in claim 1, wherein
the at least one longitudinally extending clearance groove comprises first and second clearance grooves; and
the protrusion comprises first and second axially extending rows of protrusions.

9. An ocular implant insertion apparatus as claimed in claim 1, further comprising:
first indicia on the operational portion and second indicia on the main body positioned such that the at least one clearance groove and the protrusion are aligned when the first and second indicia are aligned.

10. An ocular implant insertion apparatus as claimed in claim 1, further comprising:
a window extending through the operational portion and positioned such that the at least one clearance groove and the protrusion are aligned when the window is aligned with the at least one clearance groove.

11. An ocular implant insertion apparatus as claimed in claim 1, wherein the helical slot defines an axial length and a pitch and the pitch is substantially constant over the axial length.

12. An ocular implant insertion apparatus as claimed in claim 1, wherein the helical slot defines an axial length and a pitch and the pitch is not substantially constant over the axial length.

13. An ocular implant insertion apparatus as claimed in claim 1, wherein the protrusion defines a shape corresponding to a partial screw-thread.

14. An ocular implant insertion apparatus as claimed in claim 1, wherein the protrusion defines a curved shape.

15. An ocular implant insertion apparatus as claimed in claim 1, wherein the helical slot and the at least one longitudinally extending clearance groove define a plurality of curved corners at the intersections thereof.

16. An ocular implant insertion apparatus as claimed in claim 1, wherein the operational portion will move axially in response to the application of axial force thereto when the protrusion is within the at least one clearance groove.

17. An ocular implant insertion apparatus as claimed in claim 1, wherein the operational portion will move rotationally and axially in response to the application of rotational force thereto when the protrusion is within the helical slot.

18. An ocular implant insertion apparatus as claimed in claim 1, wherein the operational portion will not move rotationally in response to the application of rotational force thereto when the protrusion is within the clearance groove between portions of the helical slot.

19. An ocular implant insertion apparatus as claimed in claim 1, further comprising:
a lens stored in the main body.

20. An ocular implant insertion apparatus as claimed in claim 19, wherein the lens comprises an intraocular lens.

* * * * *